United States Patent [19]

Larsen

[11] Patent Number: 4,529,705

[45] Date of Patent: Jul. 16, 1985

[54] REAGENT FOR COMBINED DILUTING AND LYSING WHOLE BLOOD

[75] Inventor: Fred L. Larsen, Miami Lakes, Fla.

[73] Assignee: Coulter Electronics, Inc., Hialeah, Fla.

[21] Appl. No.: 501,028

[22] Filed: Jun. 6, 1983

[51] Int. Cl.³ .................. G01N 33/48; C09K 3/34
[52] U.S. Cl. ........................... 436/17; 436/10; 436/15; 436/18; 436/63; 436/66
[58] Field of Search ............... 436/10, 17, 18, 63, 436/15, 66

[56] References Cited

U.S. PATENT DOCUMENTS

| | | | |
|---|---|---|---|
| 3,874,852 | 4/1975 | Hamill | 436/17 |
| 4,038,389 | 7/1977 | Lamb | 424/243 |
| 4,102,810 | 7/1978 | Armstrong | 436/18 |
| 4,185,964 | 1/1980 | Lancaster | 436/17 |
| 4,213,876 | 7/1980 | Crews et al. | 436/10 |
| 4,248,634 | 2/1981 | Forester | 436/18 |
| 4,276,094 | 6/1981 | Gutnick et al. | 134/10 |
| 4,286,963 | 9/1981 | Ledis et al. | 436/17 |
| 4,297,238 | 10/1981 | Vormbrock et al. | 436/17 |
| 4,346,018 | 8/1982 | Carter et al. | 436/18 |
| 4,384,971 | 5/1983 | Carter et al. | 436/17 |
| 4,485,175 | 11/1984 | Ledis et al. | 436/63 |

FOREIGN PATENT DOCUMENTS

| | | | |
|---|---|---|---|
| 53-100298 | 9/1978 | Japan | 436/17 |
| 56-112566 | 9/1981 | Japan | 436/18 |
| 2077916 | 12/1981 | United Kingdom | 436/18 |
| 900830 | 1/1982 | U.S.S.R. | 424/243 |

*Primary Examiner*—Teddy S. Gron
*Attorney, Agent, or Firm*—Silverman, Cass & Singer, Ltd.

[57] ABSTRACT

An improved reagent provides combined diluting and lysing of whole blood for use in instruments performing electronic blood cell counting and hemoglobin determination. The reagent prevents platelet aggregation and improves the accuracy of the white blood cell count.

34 Claims, No Drawings

4,529,705

REAGENT FOR COMBINED DILUTING AND LYSING WHOLE BLOOD

BACKGROUND OF THE INVENTION

This invention relates to reagents for diluting and lysing whole blood particularly employed in automatic instruments for blood particle counting and hemoglobin determination.

In relatively simple blood particle counting instruments, for example, the HEMO-W ® instrument manufactured by Coulter Electronics, Inc. of Hialeah, Fla., measurements are limited to the simultaneous determination of hemoglobin concentration and total leukocyte count of a whole-blood specimen. In such a system, the erythrocytes are lysed (hemolyzed) to liberate their hemoglobin for quantitative determination. The white blood cells (WBC) remain as individually countable particles suited to the Coulter ® electronic-impedance method.

An individual blood sample is prepared, manually or in an automatic diluter, by addition to a combined diluting and lysing solution before aspiration into the HEMO-W ® instrument. Prior combined diluting and lysing reagents, for example, Isolyse ® manufactured by the Coulter Diagnostics Division of Coulter Electronics, Inc. have included the conventional disodium salt of ethylenadiaminetetraacetic acid (EDTA) to inhibit platelet aggregation as well as to prevent coagulation of the sample. In some instances, erroneously high WBC count has been observed with the HEMO-W ® instrument because platelet aggregations have been included in the WBC count. This problem has occurred with capillary blood samples which are obtained in small quantity by the "finger stick" method and then directly added to the combined diluting and lysing reagent in which lysing begins immediately. Artificially elevated WBC count has not occurred using venous blood samples which are conventionally added directly to a diluent and anticoagulant solution containing EDTA, prior to further addition to the combined diluting and lysing solution for aspiration into the instrument. It has been determined that the EDTA component in existing formulations of combined diluting and lysing solutions is incapable of preventing platelet aggregation under the conditions of concurrent lysing, unless the blood sample has been previously subjected to an anticoagulation agent. Once lysing of the sample has occurred, platelet aggregates will not disperse and addition of further EDTA merely promotes cohesion of the aggregates.

Multi-purpose blood diluents for use in automatic hematology instruments have been described in U.S. Pat. No. 3,962,125, U.S. Pat. No. 4,213,876 and U.S. Pat. No. 4,346,018. The multi-purpose diluents described in these patents do not include lysing agents, and are specifically formulated to stablize and preserve the red blood cells so that their volume can be accurately measured and counted in addition to counting of white blood cells. U.S. Pat. No. 4,213,876 describes the use of inorganic metalic sulfate for suppressing turbidity caused by abnormal plasma globulins or by elevated white blood cell count which can affect hemoglobin determinations.

U.S. Pat. Nos. 3,874,852 and 4,346,018 describe lysing reagents which are formulated for lysing samples which have been previously diluted for counting of red blood cells and white blood cells.

SUMMARY OF THE INVENTION

The invention provides an improved reagent for combined diluting and lysing of whole blood samples which prevents platelet aggregation and improves the accuracy of the white blood cell count. The improved diluting and lysing reagent can also contain a chromagen-forming agent for determiantion of hemoglobin concentration in the sample.

The reagent of the invention includes a quaternary ammonium salt detergent for lysing red blood cells in the sample. The reagent also includes a salt providing an anion which is effective in preventing aggregation of platelets and in dispersing platelet aggregates under conditions of concurrent lysing of the red blood cells, particularly when the blood sample has not been previously subjected to an anticoagulation agent. The effective platelet dispersing anions are provided in the reagent by salts having a sulfate, carbonate, formate or acetate anion.

DETAILED DESCRIPTION OF THE INVENTION

Broadly, the combined diluting and lysing reagent according to this invention is an aqueous solution which includes a lysing agent for stromatolysing red blood cells and platelets, and an anion component which is effective to disperse platelet aggregates under the concurrent lysing conditions. The reagent can also contain a chromagen-forming agent for determination of hemoglobin concentration.

The following table presents a preferred composition for the aqueous diluting and lysing solution embodying the invention, indicating the components and concentrations per liter of solution:

TABLE 1

| Component | Approximate Concentration |
|---|---|
| Sodium Phosphate Monobasic | 0.037 g/l |
| Sodium Phosphate Dibasic | 1.43 g/l |
| Sodium Sulfate | 14.3 g/l |
| Polyethoxylated Alkyl Phenol | 0.72 g/l |
| Cetyldimethylethylammonium Bromide | 1.1 g/l |
| Sodium Nitrite | 0.017 g/l |
| Sodium Nitroferricyanide | 0.01 g/l |
| Potassium Cyanide | 0.05 g/l |

The formulation specified above is adjusted to a preferred pH in the range 8.2 to 8.8 by the action of the phosphate buffering agents. The buffering agents are optional components in the formulation of the invention inasmuch as the deletion of the buffering agents results in a reagent having a pH of approximately 9.0 and in which the platelets can be well dispersed. Suitable pH of the reagent is in the range 7–11. The osmolality of suitable formulations according to the invention can be in the range 240 to 270 milliosmoles, preferably 255 milliosmoles.

The preferred lysing agents in the reagent stromatolysing red blood cells and platelets are the quaternary ammonium salt detergents. Suitable quaternary ammonium salts employed as lysing agents are of the type having attached to nitrogen 3 short chain alkyl groups having 1 to 6 carbon atoms, preferably 1–3 carbon atoms, and one long chain alkyl group having 10 to 18 carbon atoms, as more fully described in U.S. Pat. No. 4,346,018 which is incorporated by reference. Particularly preferred quaternary ammonium salts employed as lysing agents include cetydimethylethylammonioum bromide (Bretol ®) and tetradecyltrimethylammonium bromide (Mytab ®) commercially available from Hexcel, Inc. Alternative conventional lysing agents such as Triton X-100 manufactured by Rohm and Haas, Inc. and Saponin manufactured by Coulter Electronics, Inc. can be employed but are not as effective as quaternary ammonium salt detergents in the lysing of the red cells.

The quaternary ammonium salts can be employed in the aqueous solution in a concentration within the range of approximately 0.5 to 10 grams per liter, preferably 1 to 3 grams per liter, when a preferred dilution of approximately one part whole blood to a total volume of 500 parts of diluted blood is employed with the combined diluting and lysing reagent. It will be understood that different concentration of the lysing agent can be employed in the combined diluting and lysing reagent where previous dilution of the blood sample is to be employed.

The anion components of the combined diluting and lysing reagent which have been found to be effective to disperse platelet aggregates under the concurrent lysing condition include sulfate, carbonate, formate and acetate. Unlike the conventional EDTA anticoagulation component of prior art reagents for combined diluting and lysing of whole blood, these anions can prevent platelet aggregation and disperse platelet aggregates already formed prior to the lysing of the blood sample.

These platelet dispersing anions can be employed in the reagent in a concentration within the range of approximately 30 to 180 millimoles per liter (mmole/l) preferably within the range 60 to 120 mmole/l. These anions can be provided by salts having preferred cations including sodium, potassium, and ammonium. Magnesium and calcium cations and organic cations such as tris(hydroxmethyl)aminomethyl are less favored than the preferred cations and generally require addition of suitable electrolyte such as sodium chloride for satisfactory electronic WBC counting. The particularly preferred platelet dispersing anions are provided by salts which include sodium sulfate, potassium sulfate, sodium carbonate and potassium carbonate which are particularly effective in eliminating platelet aggregates when the total concentration of these salts, and similarly the anions, in the reagent is in the preferred range 60–100 mmole/liter and employing the above-described 1:500 dilution ratio. In contrast, sodium nitrate and sodium phosphate have been found to be entirely ineffective in preventing platelet aggregates with concurrent lysing.

The combined diluted lysing reagent of the invention can additionally contain alkali metal cyanide, for example potassium cyanide, when hemoglobin determination is obtained using the same blood sample. Optionally, additional cyanide can be provided by an alkali metal ferricyanide such as sodium nitroferricyanide. The cyanide ion reacts with hemoglobin to produce the stable chromogen, cyanmethemoglobin, which can be measured photometrically in the HEMO-W ® instrument, typically at 525 nm. The potassium cyanide concentration can be in the range 0.005 to 0.6 gram/liter, preferably 0.05 gram/liter at the preferred reagent pH of apprioximately 8.5.

Suitable surfactants can optionally be included in the reagent of the invention in order to prevent the accumulation of proteinaceous deposits within the aperture of the electronic counting instrument as well as helping to maintain the size of the white blood cells. Suitable surfactants for such purpose in the reagent include the nonionic surfactants, for example, polyoxyethylated alkylphenols, poly(oxypropylene) poly(oxyethylene) condensates, and polyethylene glycol p-isoalkylphenyl ethers such as those surfactants commercially available under the trade name Diazopon TM manufactured by GAF Corporation. While these surfactants are not essential to the effectiveness of the reagent, they can be employed in concentrations in the range 0.1 to 5 grams per liter, preferably about 0.7 gram per liter.

Sodium nitrite is considered an inactive ingredient in the reagent of the invention, but can be included in a preferred formulation of the reagent as indicated in Table 1.

The following examples are illustrative of the reagents of the invention and their use, but do not indicate limitation upon the scope of the claims.

EXAMPLE 1

A reagent was prepared according to the formulation presented in Table 1 in distilled water at 22° C., with the order of addition of components as listed. The pH of the formulation was approximately 8.5 and the osmolality was approximately 255 mOsm. The combined lysing and diluent was then used to dilute whole blood samples. A capillary blood sample obtained by "finger stick" was drawn into a 20 uL pipette and diluted into 10 mLs. of the reagent for simulation of the use of Isopet ® microcollection system. The resulting diluted sample began lysing and was allowed to stand at room temperature for approximately 2 minutes prior to aspiration into the cuvette of the HEMO-W ® instrument. In order to monitor the volume size distribution of the white blood cells, a C-1000 Channelyzer ® (Coulter Electronics, Inc.) equipped with an X-Y plotter was connected to test point 1 of the HEMO-W ® instrument. The results showed nearly complete absence of any debris in the 30 to 50 um$^3$ region indicating that platelet aggregates had been effectively dispersed. Both the total white blood cell count and hemoglobin value accurately corresponded to the references.

EXAMPLE 2

A reagent was prepared as described in Example 1 with the exception that 100 millimoles of potassium sulfate was substituted for sodium sulfate in the formulation presented in Table 1. The reagent was employed with the same diluting and monitoring procedure described in Example 1 with the result that the potassium sulfate was equally effective as sodium sulfate in dispersing platelet aggregates.

EXAMPLE 3

A reagent was prepared as described in Example 1 with the exception that 100 millimoles of tris(hydroxmethyl)aminomethyl sulfate was substituted for sodium sulfate in the formulation presented in Table 1 and 50 millimoles of sodium chloride was added in addition. The reagent was employed with the same diluting and monitoring procedure described in Example 1 with the result that the tris sulfate was equally effective as sodium sulfate in dispersing platelet aggregates.

EXAMPLE 4

A reagent was prepared as described in Example 1 with the exception that 100 millimoles of ammonium sulfate was substituted for sodium sulfate in the formulation presented in Table 1. The reagent was employed with the same diluting and monitoring procedure described in Example 1 resulting in a minimal amount of debris in the 30–50 um$^3$ region indicating that ammonium sulfate was not as effective as sodium sulfate in dispersng platelet aggregates.

EXAMPLE 5

A reagent was prepared as described in Example 1 with the exception that 70 millimoles of sodium carbonate was substituted for sodium sulfate in the formulation presented in Table 1. The reagent was employed with the same diluting and monitoring procedure described in Example 1 with the result that sodium carbonate was equally effective as sodium sulfate in dispersing platelet aggregates.

EXAMPLE 6

A reagent was prepared as described in Example 1 with the exception that 70 millimoles of sodium formate was substituted for sodium sulfate in the formulation presented in Table 1. The reagent was employed with the same diluting and monitoring procedure described in Example 1, resulting in white blood cell counts and hemoglobin data matching the references even though some platelet debris was discernable.

EXAMPLE 7

A reagent was prepared as described in Example 1 with the exception that 70 millimoles of sodium acetate was substituted for sodium sulfate in the formulation presented in Table 1. The reagent was employed with the same diluting and monitoring procedure described in Example 1, resulting in aceptable white blood cell count and hemoglobin data in comparison to the references even though some platelet debris was discernable.

I claim:

1. A reagent for combined diluting and lysing a whole blood sample for use in electronic enumeration of white blood cells and determination of hemoglobin concentration, comprising in an aqueous solution:
   (A) a quaternary ammonium salt detergent for lysing red blood cells in the sample;
   (B) at least one salt of an anion selected from the group consisting of sulfate, carbonate, formate, and acetate for preventing aggregation of platelets in said sample; and
   (C) an alkali metal cyanide for conversion of hemoglobin to a chromagen.

2. The reagent as claimed in claim 1 wherein said salt includes at least one cation selected from the group consisting of sodium, potassium, ammonium, magnesium, calcium, and tris(hydroxymethyl)aminomethyl.

3. The reagent as claimed in claim 1 wherein said salt is selected from the group consisting of sodium sulfate, potassium sulfate, ammonium sulfate, magnesium sulfate, calcium sulfate, and tris(hydroxymethyl)aminomethyl sulfate.

4. The reagent as claimed in claim 3 wherein the concentration of sulfate ion is in the range 30 to 180 mmole/liter.

5. The reagent as claimed in claim 3 wherein the concentration of sulfate ion is in the range 60–120 mmole/liter.

6. The reagent as claimed in claim 1 wherein said salt includes sodium sulfate.

7. The reagent as claimed in claim 6 wherein the concentration of sulfate ion is in the range 30 to 180 mmole/liter.

8. The reagent as claimed in claim 6 wherein the concentration of sulfate ion is in the range 60–100 mmole/liter.

9. The reagent as claimed in claim 1 wherein said salt includes at least one member selected from the group consisting of sodium carbonate, potassium carbonate, ammonium carbonate, magnesium carbonate, calcium carbonate, and tris(hydroxymethyl)aminomethyl carbonate.

10. The reagent as claimed in claim 1 wherein the concentration of said anion is in the range 30 to 180 mmole/liter.

11. The reagent as claimed in claim 1 wherein said cyanide includes potassium cyanide.

12. The reagent as claimed in claim 11 wherein said potassium cyanide concentration is in the range 0.005 to 0.65 g/liter.

13. The reagent as claimed in claim 1 further comprising phosphate buffering agent.

14. The reagent as claimed in claim 13 wherein said phosphate buffering agent includes a monobasic phosphate salt and a dibasic phosphate salt.

15. The reagent as claimed in claim 1 wherein said reagent has a pH in the range 7 to 11.

16. The reagent as claimed in claim 1 wherein said quaternary ammonium detergent includes at least one member selected from the group consisting of cetyldimethylethylammonium bromide and tetradecyltrimethylammonium bromide.

17. The reagent as claimed in claim 1 comprising the following components and the concentrations indicated per liter of the solution:

| Component | Concentration |
| --- | --- |
| Sodium Phosphate Monobasic | 0.037 g/l |
| Sodium Phosphate Dibasic | 1.43 g/l |
| Sodium Sulfate | 14.3 g/l |
| Polyethoxylated Alkyl Phenol | 0.72 g/l |
| Cetyldimethylethylammonium Bromide | 1.1 g/l |
| Sodium Nitrite | 0.017 g/l |
| Sodium Nitroferricyanide | 0.01 g/l |
| Potassium Cyanide | 0.05 g/l |

18. A reagent for combined diluting and lysing a whole blood sample for use in electronic enumeration of white blood cells and determination of hemoglobin concentration, free from EDTA and consisting essentially of the following components in an aqueous solution:
   (A) a quaternary ammonium salt detergent for lysing red blood cells in the sample;
   (B) at least one salt of an anion selected from the group consisting of sulfate, carbonate, formate, and acetate for preventing aggregation of platelets in said sample; and
   (C) an alkali metal cyanide for conversion of hemoglobin to a chromagen.

19. The reagent as claimed in claim 18 wherein said salt includes at least one cation selected from the group consisting of sodium, potassium, ammonium, magnesium, calcium, and tris(hydroxymethyl)aminomethyl.

20. The reagent as claimed in claim 18 wherein said salt is selected from the group consisting of sodium sulfate, potassium sulfate, ammonium sulfate, magnesium sulfate, calcium sulfate, and tris(hydroxymethyl)aminomethyl sulfate.

21. The reagent as claimed in claim 20 wherein the concentration of sulfate ion is in the range 30 to 180 mmole/liter.

22. The reagent as claimed in claim 20 wherein the concentration of sulfate ion is in the range 60–120 mmole/liter.

23. The reagent as claimed in claim 18 wherein said salt includes sodium sulfate.

24. The reagent as claimed in claim 23 wherein the concentration of sulfate ion is in the range 30 to 180 mmole/liter.

25. The reagent as claimed in claim 23 wherein the concentration of sulfate ion is in the range 60–100 mmole/liter.

26. The reagent as claimed in claim 18 wherein said salt includes at least one member selected from the group consisting of sodium carbonate, potassium carbonate, ammonium carbonate, magnesium carbonate, calcium carbonate, and tris(hydroxymethyl)aminomethyl carbonate.

27. The reagent as claimed in claim 18 wherein the concentration of said anion is in the range 30 to 180 mmole/liter.

28. The reagent as claimed in claim 18 wherein said cyanide includes potassium cyanide.

29. The reagent as claimed in claim 28 wherein said potassium cyanide concentration is in the range 0.005 to 0.65 g/liter.

30. The reagent as claimed in claim 18 further including phosphate buffering agent.

31. The reagent as claimed in claim 30 wherein said phosphate buffering agent includes a monobasic phosphate salt and a dibasic phosphate salt.

32. The reagent as claimed in claim 18 wherein said reagent has a pH in the range 7 to 11.

33. The reagent as claimed in claim 18 wherein said quaternary ammonium detergent includes at least one member selected from the group consisting of cetyldimethylethylammonium bromide and tetradecyltrimethylammonium bromide.

34. The reagent as claimed in claim 18 consisting essentially of the following components and the concentrations indicated per liter of the solution:

| Component | Concentration |
|---|---|
| Sodium Phosphate Monobasic | 0.037 g/l |
| Sodium Phosphate Dibasic | 1.43 g/l |
| Sodium Sulfate | 14.3 g/l |
| Polyethoxylated Alkyl Phenol | 0.72 g/l |
| Cetyldimethylethylammonium Bromide | 1.1 g/l |
| Sodium Nitrite | 0.017 g/l |
| Sodium Nitroferricyanide | 0.01 g/l |
| Potassium Cyanide | 0.05 g/l |

* * * * *